United States Patent [19]
Alving et al.

[11] Patent Number: 5,820,880
[45] Date of Patent: Oct. 13, 1998

[54] LIPOSOMAL FORMULATION

[75] Inventors: Carl R. Alving, Bethesda; Jean M. Muderhwa, Silver Spring, both of Md.

[73] Assignees: The United States of America as represented by the Secretary of the Army, Washington, D.C.; Jenner Technologies, Danville, Calif.

[21] Appl. No.: 480,563

[22] Filed: Jun. 7, 1995

[51] Int. Cl.[6] .......................... A61K 9/127; A61K 33/06; A61K 39/385; A61K 9/66
[52] U.S. Cl. ................... 424/450; 424/184.1; 424/277.1; 424/278.1; 424/283.1; 436/829; 514/2; 514/885; 514/964
[58] Field of Search .................. 424/450, 184.1, 424/277.1, 278.1, 283.1; 514/885, 964, 2; 436/829

[56] References Cited

U.S. PATENT DOCUMENTS

| | | | |
|---|---|---|---|
| 4,897,269 | 1/1990 | Mezei | 424/450 |
| 5,013,555 | 5/1991 | Collins | 424/450 |
| 5,053,217 | 10/1991 | Lehigh | 424/450 |
| 5,374,548 | 12/1994 | Caras | 424/450 |

FOREIGN PATENT DOCUMENTS 9401645  1/1995  South Africa .

OTHER PUBLICATIONS

White, W.I., et al., "Antibody and cytotoxic T–lymphocyte responses to a single liposome–associated peptide antigen," *Vaccine* (1995) 13(12):1111–1122.

*Primary Examiner*—Anthony C. Caputa
*Attorney, Agent, or Firm*—Morrison & Foerster LLP

[57] ABSTRACT

Depending on the antigen encapsulated, liposomal formulations are subject to instability in the presence of alum. Formulations containing a nonionic detergent as a stabilizing agent avoid this instability.

8 Claims, 8 Drawing Sheets

LIPOSOMAL FORMULATION

FIELD OF THE INVENTION

The invention relates to pharmaceutical formulations, especially liposomal formulations. More specifically, the invention concerns a method to stabilize liposomes administered in the presence of an aluminum adjuvant compound.

BACKGROUND ART

Formulation of vaccines by encapsulating the antigen/immunogen in liposomes represents an approach that has been widely used. It is often desirable to include, along with the liposome-encapsulated antigen, an adjuvant containing an aluminum salt (i.e., an alum) such as aluminum hydroxide. It has been observed that in some cases alum greatly stimulates the immunogenicity of the antigen while in others it either has no effect or inhibits the immune response. The nature of the effect observed appears to depend on the nature of the antigen. Antibody production is enhanced in rabbits injected with liposomes containing lipid A and malaria antigen R32tet32 when the liposomes are adsorbed to alum (unpublished observations). However, an HIV peptide encapsulated in liposomes exhibited decreased immunogenicity when alum was included in the formulation (White, W. I. et al. *Vaccine* (1995) in press. A similar composition containing the RLF malaria antigen was not affected by the presence of alum (unpublished observations).

It would be desirable to prepare the liposome formulation in such a way that administration with alum would consistently enhance the immune response. The present invention describes such formulations and also provides a means to predict, for a given antigen, whether or not the improved composition will be desirable or necessary.

DISCLOSURE OF THE INVENTION

It has now been found, surprisingly, that the presence of an alum adjuvant disrupts liposomes containing certain antigens. Prevention of this disruption stabilizes and maintains the immunogenicity of the composition. Furthermore, measurement of the ability of a particular formulation to undergo disruption in the presence of alum provides a predictive tool for determining whether alum will or will not diminish the immunogenicity of the composition.

Thus, in one aspect, the invention is directed to a pharmaceutical composition comprising at least one antigen encapsulated in liposomes, along with a stabilizing agent effective to prevent the disruption of the liposomes which would otherwise occur in the presence of alum. The stabilizer is a nonionic detergent. The structural characteristics of the nonionic detergent are such that it mimics the interactive properties of certain polyoxyethylene sorbitan esters, commercially known as "Tweens." The esterified form of the Tween must contain less than 18 carbons in the acyl group and/or at least one π-bond.

MODES OF CARRYING OUT THE INVENTION

Figure 1A:
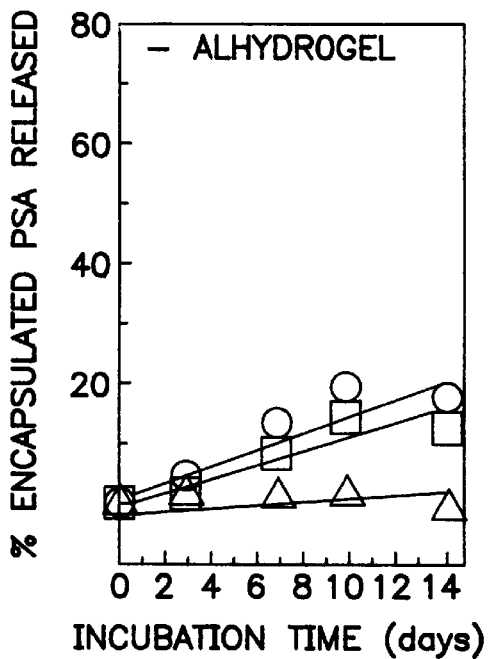
FIG. 1*a* is a graphic representation of the rate of release of PSA from liposomes in the absence of added alum.

The invention provides a method to stabilize liposomal preparations against disruption caused by the presence of aluminum hydroxide gels or other alum-based adjuvants. The present applicants have found that the varying effect of the addition of alum adjuvants on the immunogenicity of liposomal preparations is due to an effect of the alum on the integrity of the liposomes per se. Therefore, in addition to providing a method to stabilize those preparations that will be disrupted in the presence of alum, the invention provides a method to predict the effect of the addition of alum adjuvants on the immunogenicity of a given composition.

The composition can be assayed in vitro in the presence and absence of an alum adjuvant for release of the substance encapsulated in the liposomes. The assay employed to detect this release will, of course, depend on the nature of the substance encapsulated; the release of glucose and PSA are exemplified below, but the method of assay will be one appropriate to a particular substance in question. For example, if the encapsulated substance is a cytokine, the concentration of the cytokine entrapped in the liposomes and released can be compared by measuring proliferative activity against target cells. If the entrapped substance is an enzyme, the released enzyme activity can be assessed. The precise protocols for assessing the rate of release of an encapsulated substance do not form part of the invention; these are standard in the art and specific for the substance in question.

However, the results of this assay, the inventors have found, are predictive of the behavior of the composition tested in vivo. Compositions which show enhanced rates of release in the presence of alum in vitro will show reduced immunogenicity in vivo; however, both the enhanced release rate and reduced immunogenicity can be alleviated according to the method of the invention.

Especially for those compositions shown in the in vitro assay to be subject to disruption by alum, and thus potentially having reduced immunogenicity, the invention provides a remedy. The compositions can be stabilized by including, in the liposomal composition, a stabilizing agent which will effectively prevent the disruption of liposomes by contact with the adjuvant. The liposomes are formulated by using a stabilizing agent, typically a nonionic detergent corresponding to the properties of Tween 80. These properties are generated by detergent structures which contain polyoxyethylene side chains and which are free of saturated long-chain hydrophobic side chains. Thus, preferred nonionic detergent for inclusion in the liposomal preparations of the invention include Tween 20, Tween 40, Tween 80 and Tween 85.

As is generally known, liposomes are unilamellar or multilamellar structures wherein an aqueous medium is surrounded by a lipid bilayer. The composition of the lipid bilayer, forming the structural basis for the liposome is generally composed at least of phospholipids, and more generally of mixtures of phospholipids with lipids per se. In the liposomes most useful in the present invention, phosphatidylcholine derivatives, phosphatidylglycerol derivatives and the like are used along with non phospholipid components, if desired, such as cholesterol. Suitable alternative embodiments include mixtures of phospholipids with, for example, triglycerides. In addition, fatty acids, lipid vitamins, steroids, lipophilic drugs and other lipophilic compounds that can be included in a stable lipid bilayers which either do or do not include phospholipids can be used. Liposomes in general are referred to as smectic mesophases.

In more detail, liposomes, as they are ordinarily used, consist of smectic mesophases and may consist of either phospholipid or nonphospholipid smectic mesophases or mixture thereof. Smectic mesophases are intermediate states between solid and liquid, commonly known as liquid crystals. These states are characterized by residual order in some directions but not in others. In general, the molecules contained are somewhat longer than wide and have a polar or aromatic portion. The molecular shape and the polar-polar or aromatic interactions permit the molecules to align in partially ordered arrays, especially when the molecules possess a polar group at one end. Liquid crystals with long-range order in the direction of the long axis of the molecules contained are called smectic, layered or lamellar liquid crystals. In smectic states, the molecules may be in single or double layers, normal or tilted to the plane of the layer and with frozen or melted aliphatic chains.

In the liposomes employed in the present invention, phospholipids are included and the liposomes may carry a net positive charge, a net negative charge or can be neutral. Inclusion of diacetylphosphate is a convenient method for conferring negative charge; stearylamine can be used to provide a positive charge. Preferably, the lipids are diacylglycerols wherein at least one acyl group comprises at least 12C, preferably between 14–24C. It is also preferred that at least one head group of the phospholipids—i.e., the portion of the molecule containing the phosphate group—is a phosphocholine, a phosphoethanolamine, a phosphoglycerol, a phosphoserine, or a phosphoinositol.

Stock solutions of lipids in chloroform or chloroform/methanol can be stored at about −20° C. Preferably, chloroform is used as the only solvent since it is more readily evaporated than methanol.

Phospholipids may be obtained from natural sources, such as egg or soybean phosphatidylcholine, brain phosphatidic acid, brain or plant phosphatidylinositol, heart cardiolipin, or plant or bacterial phosphatidylethanolamine. However, these are preferably not used as the primary phosphatides—i.e., constituting more than 50% of the total phosphatide composition. It is preferred to use commercially available, relatively pure phospholipids.

In the present invention, liposomes may comprise lipids in any molar ratio and optionally contain cholesterol. Preferably, DMPC, DMPG and cholesterol are combined at molar ratios of about 0.9:0.1:0.75.

As used herein, the term "liposomal lipid mixture" refers to those components which make up the structural portion, i.e., the lipid bilayer, of the liposome encapsulating the substance contained in aqueous medium enclosed therein.

There are a number of methods available for making liposomes; the size depends on the method chosen. Generally, liposomes suspended in aqueous solution are spherical and have one or several concentric lipid bilayers. Each monolayer consists of a parallel array of molecules represented by the formula XY wherein X is hydrophilic and Y is hydrophobic; in aqueous solution the concentric layers are arranged such that the hydrophilic moieties remain in contact with aqueous phase and hydrophobic regions self-associate. When aqueous phases are present both inside and outside the liposome, the lipid molecules form a bilayer, known as a lamella, of the arrangement XY-YX.

Typically, liposomes are prepared by mixing the phospholipid and other components which form part of the structure of the liposome in an organic solvent, evaporating off the solvent, resuspending in agueous solvent, and finally lyophilizing the lipid/phospholipid composition. The lyophilized composition is then reconstituted in a buffer containing the substance to be encapsulated.

In a particularly preferred method, the liposomes are prepared by mixing the liquids to be used, including lipid A, in the desired proportion in a container such as a glass pear-shaped flask having a volume ten times greater than the anticipated suspension of liposomes. Using a rotary evaporator, the solvent is removed at approximately 40° C. under negative pressure. The vacuum obtained from a filter pump aspirator attached to a water faucet may be used. The solvent is normally removed within about 2–5 minutes. The composition may then be dried further in a desiccator under vacuum, and is stable for about one week.

The dried lipids may be rehydrated at approximately 30 mM phospholipid in sterile, pyrogen-free water by shaking until all lipid film is off the glass. The aqueous liposomes can then be separated in aliquots, lyophilized and sealed under vacuum.

Alternatively, liposomes can be prepared according to the method of Bangham et al. *J Mol Biol* (1965) 13: 238–252; or as described by Gregoriadis in *Drug Carriers in Biology and Medicine*, G. Gregoriadis, Ed. (1979) pp. 287–341; or by the method of Deamer and Uster as described in *Liposomes*, M. Ostro, Ed. (1983); or by the reverse-phase evaporation method described by Szoka et al. *Proc Natl Acad Sci USA* (1978) 75: 4194–4198. Depending on the choice of method, the resulting liposomes will have various abilities to entrap aqueous material and differ in their space-to-lipid ratios.

The stabilizing agent can be included in the compositions of the invention either by adding the appropriate proportion of the stabilizing agent in the preparation of a lyophilized lipid mixture, or by adding the stabilizing agent to the reconstitution buffer. The stabilizing agent can be added as a single detergent or can, of course, be added as a mixture of appropriate detergents.

The proportion of the stabilizing agent to be included in the original phospholipid/lipid mixture or the concentration of the stabilizing agent in the reconstituting buffer will depend on the nature of the substance to be encapsulated and can be optimized using routine experimentation. In general, the stabilizing agent will be present at about 0.2–5 mole % based on the liposomal lipid mixture, preferably about 0.5–4 mole %.

The stabilizing agent itself will be a nonionic detergent with appropriate physical characteristics. Specifically, the nonionic detergent must be soluble at a temperature that does not adversely affect the integrity of the liposomes and that does not denature or otherwise interfere with the immunogencity of the antigen. Thus, the detergent must be soluble at a reasonable temperature. It is believed that the inability of Tween 60 and Tween 65 illustrated below to stabilize the liposome preparations in the examples described is due to their insolubility at reasonable temperatures. The general characteristics of the detergent are characterized by the Tween series provided adequate solubility properties are present.

The following examples are intended to illustrate, but not to limit the invention.

EXAMPLE 1

Preparation of Liposomes

Liposomes encapsulating either glucose or prostate-specific antigen (PSA) were prepared according to the procedure of Alving, C. R. et al. in *Liposome Technology: Interactions of Liposomes with the Biological Milieu* (1993) *III:* CRC Press, Boca Raton, Fla., pp. 317– 343. Additional descriptions are found in Verma, J. N. et al. *Infect Immun* (1992) 60: 2438–2444, and in Richards, R. L. et al. *Infect Immun* (1988) 56: 682–686. Table 1 below shows abbreviations used for the components employed in these Examples.

TABLE 1

| Abbrev. | Name | No. Carbons in each acyl | No. π-bonds in each acyl |
|---|---|---|---|
| DLPC | dilauroyl phosphatidylcholine | 12 | 0 |
| DMPC | dimyristoyl phosphatidylcholine | 14 | 0 |
| DPPC | dipalitoyl phosphatidylcholine | 16 | 0 |
| DSPC | distearoyl phosphatidylcholine | 18 | 0 |
| DOPC | dioleoyl phosphatidylcholine | 18 | 1 |
| DLnPC | dilinoleoyl phosphatidylcholine | 18 | 2 |
| DMPG | dimyristoyl phosphatidylglycerol | 14 | 0 |
| CHOL | cholesterol | | |
| LA | Lipid A | | |
| Tween 20 | polyoxyethylene sorbitan monolaurate | 12 | 0 |
| Tween 40 | polyoxyethylene sorbitan monopalmitate | 16 | 0 |
| Tween 60 | polyoxyethylene sorbitan monostearate | 18 | 0 |
| Tween 65 | polyoxyethylene sorbitan tristearate | 18 | 0 |
| Tween 80 | polyoxyethylene sorbitan monooleate | 18 | 1 |
| Tween 85 | polyoxyethylene sorbitan trioleate | 18 | 1 |
| Span 80 | sorbitan monooleate | | |

In a typical preparation, multilamellar liposomes are made from a mixture of DMPC:DMPG:CHOL:LA in a molar ratio of 9:1:7.5:0.011. The lipid A is included as an adjuvant. The lipid mixture is rotary evaporated to a dry thin film at approximately 40° C. in vacuo from a chloroform solution in a pear-shaped flask. To ensure complete removal of the organic solvent, the flask is then dried under very low vacuum (about 0.05 mm Hg) overnight in a desiccator at room temperature. After drying, the lipids are carefully swollen in deionized, sterile pyrogen-free water by vortexing. The resulting suspension is frozen at −55° C., lyophilized at −20° C. overnight and 0° C.–10° C. the following day using the Virtis Unitop 800SL Freeze Mobile (the Virtis Company, Gardener, N.Y.).

The lyophilized lipids are then reconstituted in the presence of the substance to be encapsulated to obtain multilamellar liposomes containing this substance. Glucose was encapsulated in the liposomes for ease in assessing leakage; PSA was encapsulated in the liposomes to determine the effect of the nature of the encapsulated substance on leakage. The reconstituting buffer was phosphate-buffered saline (PBS) or Tris-glycine/NaCl/Tween 80 (TG). This latter buffer was used to include the stabilizing agent, in this case Tween 80. In subsequent examples when alternative stabilizer candidates are added, these stabilizer candidates are substituted for Tween 80 in the buffer. The liposomal phospholipid concentration in the reconstituting buffer is 10–200 mM.

Unencapsulated substance (glucose or PSA) is removed by washing the liposomes three times with 0.15M NaCl at 27000×g for 10 minutes at 10° C. The resulting liposomes are suspended either in 0.15M NaCl or an appropriate isotonic buffer to reach a final phospholipid concentration of 10–200 mM.

EXAMPLE 2

Effect of Aluminum Hydroxide Gels on Liposome Integrity

For determination of liposome integrity, trapped glucose was first calculated by subtracting entrapped glucose from total glucose in the reconstitution step. Total and entrapped glucose were measured as described by Kinsky, S. C. *Methods Enzymol* (1974) 32: 501–513; Alving, C. R. et al. (1993) (supra) by measuring the change in absorbance at 340 nm in the presence of hexokinase and glucose-6-phosphate dehydrogenase. Glucose release was measured in the same way as a function of time at various temperatures in the presence and absence of alum.

Liposomes containing glucose prepared as in Example 1 were incubated with and without various commercially available aluminum hydroxide gels in a 1/1 (v/v) ratio. Alhydrogel™ and Rehydrogel™ are available from Reheis, Inc., Berkeley Heights, N.J.; Rehsorptar™ absorptive gel is supplied by Armour Pharmaceutical Company, Kankakee, Ill.

When no alum was added only about 0.06% of trapped glucose was released after 120 hours. However, when aluminum hydroxide gel was mixed with the liposomal preparations, glucose was released linearly with time in a temperature-dependent manner at various rates depending on the choice of alum. Table 2 summarizes the initial velocities for release of trapped glucose in the presence of the various aluminum hydroxide gels from the liposomes prepared in Example 1 incubated at 100 mM phospholipid mixed with 1/1 (v/v) ratio with aluminum hydroxide dosed at 2 mg aluminum/ml prior to incubation.

TABLE 2

Release of Glucose

| Type of aluminum compound tested | $V_{max}$ ($\mu$mole min$^{-1}$ × 10$^6$) | | |
|---|---|---|---|
| | 4° C. | Room Temperature (24° C.–27° C.) | 37° C. |
| Alhydrogel ™ | 8.67 | 15.10 | 23.35 |
| Rehydragel | 6.69 | 11.50 | 25.70 |
| Rehsorptar | 2.92 | 3.85 | 9.69 |

These data confirm the influence of temperature and the nature of the alum preparation on rate of release.

EXAMPLE 3

Effect of Encapsulated Substance on Liposome Stability

Liposomes were prepared according to Example 1 containing PSA as the encapsulated substance. PSA concentrations in liposomes were determined by a modification of the assay of Lowry, O. H. et al. *J Biol Chem* (1951) 193: 265–275 as described by Alving, C. R. et al. (1993) (supra). Released PSA was determined using a standard Lowry protein assay.

Briefly, the assay for PSA in liposomes is modified to include sequential addition of chloroform to an aliquot of liposome sample, evaporating the sample to dryness in a Speed Vac Concentrator SC100 (Savant Instruments, Inc., Farmingdale, N.Y.) at 43° C. or under a stream of nitrogen, adding 15% sodium deoxycholate in normal saline, and vortexing to ensure that all protein in the sample is dissolved. The sodium deoxycholate-sample solution is then processed for the standard Lowry protein assay. After 20 minutes incubation, the sample is centrifuged at 27000×g for 10 minutes and the supernatant is collected and absorbance read at 750 nm.

Using the foregoing assays, the encapsulation efficiency for PSA was found to be 50%.

Figure 1B:
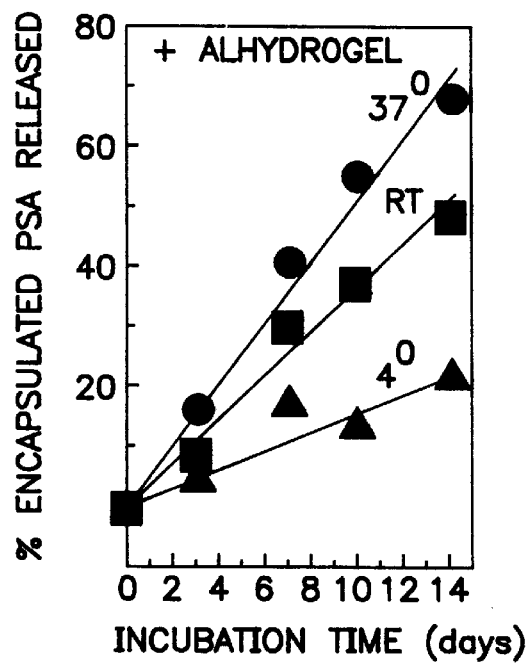
FIG. 1*b* is a representation of the rate of release of PSA from liposomes in the presence of alum.
Figure 1C:
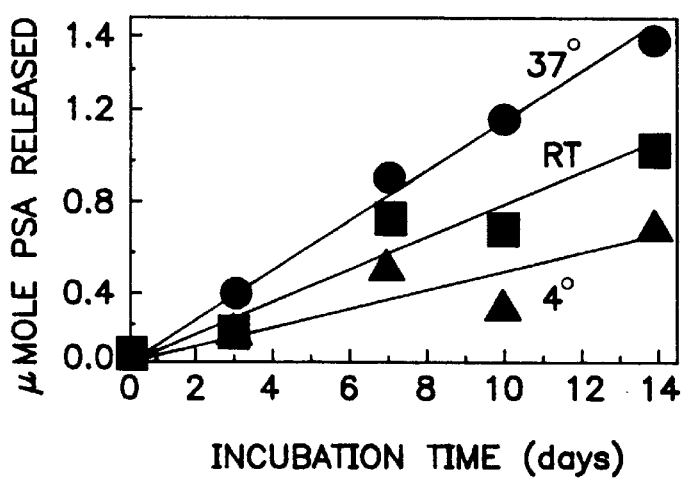
FIG. 1*c* represents the results of FIG. 1*b* corrected for the release rates shown in FIG. 1*a*.
Figure 2B:
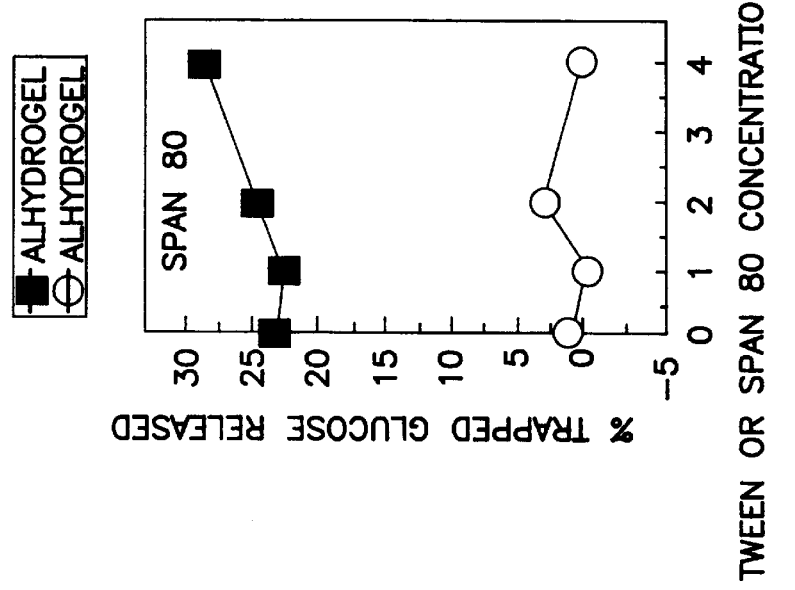
FIG. 2*b* shows the effect of Span 80 concentration in liposomes on the release of glucose in the presence and absence of alum.
Figure 2A:
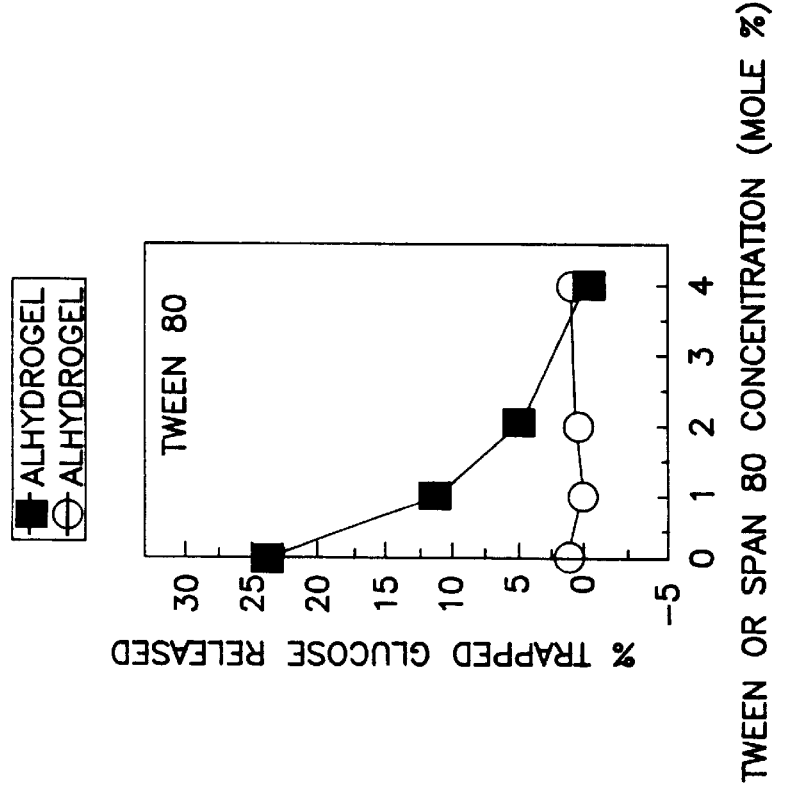
FIG. 2*a* shows the effect of Tween 80 concentration in liposomes on the release of glucose in the presence and absence of alum.
Figure 2D:
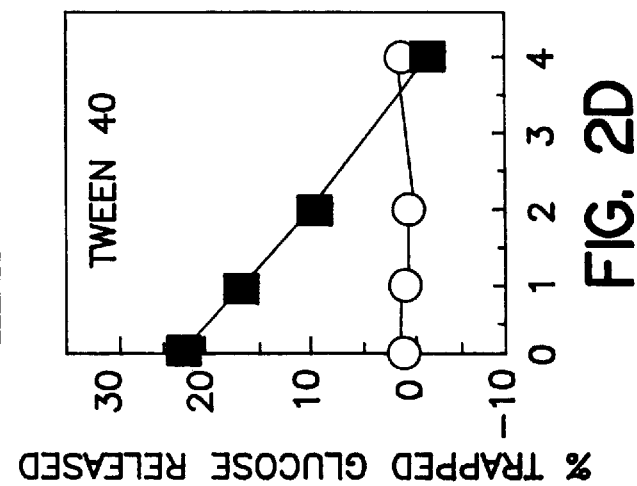
FIG. 2*d* shows the effect of Tween 40 concentration in liposomes on the release of glucose in the presence and absence of alum.
Figure 2C:
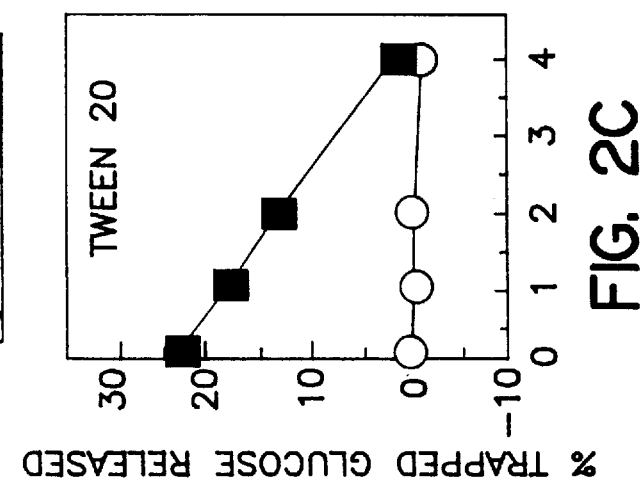
FIG. 2*c* shows the effect of Tween 20 concentration in liposomes on the release of glucose in the presence and absence of alum.
Figure 2F:
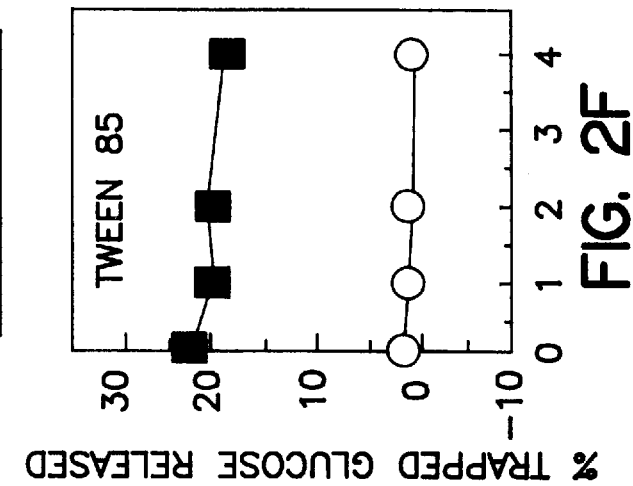
FIG. 2*f* shows the effect of Tween 65 concentration in liposomes on the release of glucose in the presence and absence of alum.
Figure 2E:
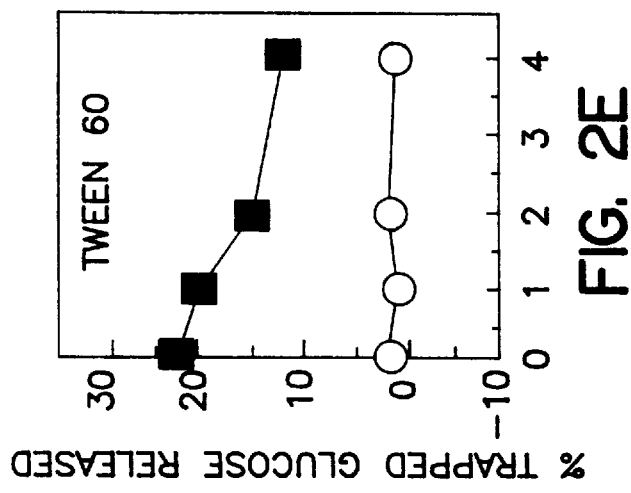
FIG. 2*e* shows the effect of Tween 60 concentration in liposomes on the release of glucose in the presence and absence of alum.
Figure 2G:
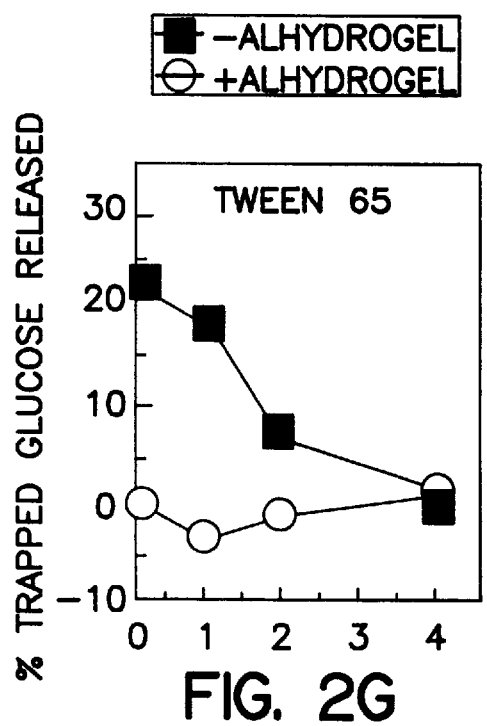
FIG. 2*g* shows the effect of Tween 85 concentration in liposomes on the release of glucose in the presence and absence of alum.
Figure 3:
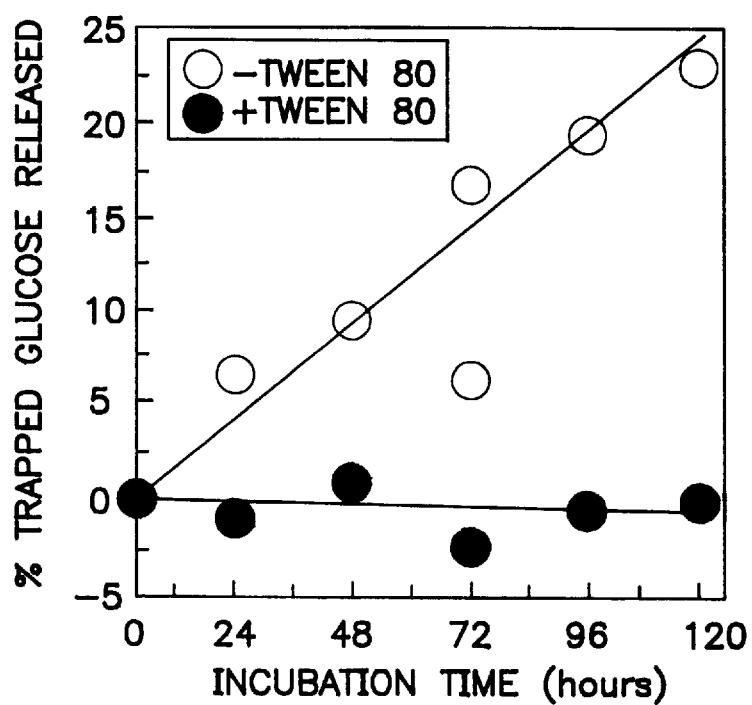
FIG. 3 shows the time course of release of glucose from liposomes in the presence of Alhydrogel™ for liposomes prepared with and without Tween 80.
Figure 4B:
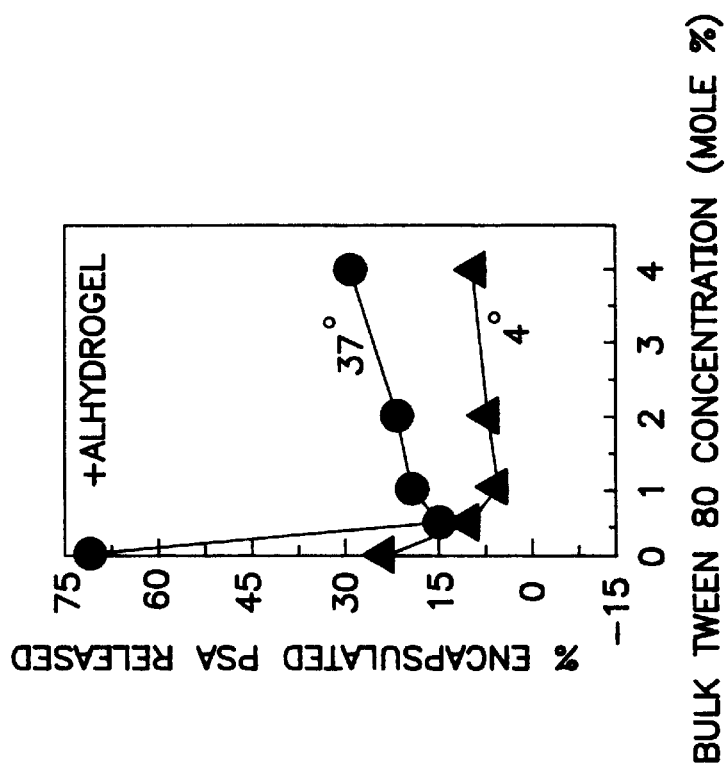
FIG. 4*b* shows the effect of Tween 80 concentration on release of PSA from liposomes at two temperatures in the presence of alum.
Figure 4A:
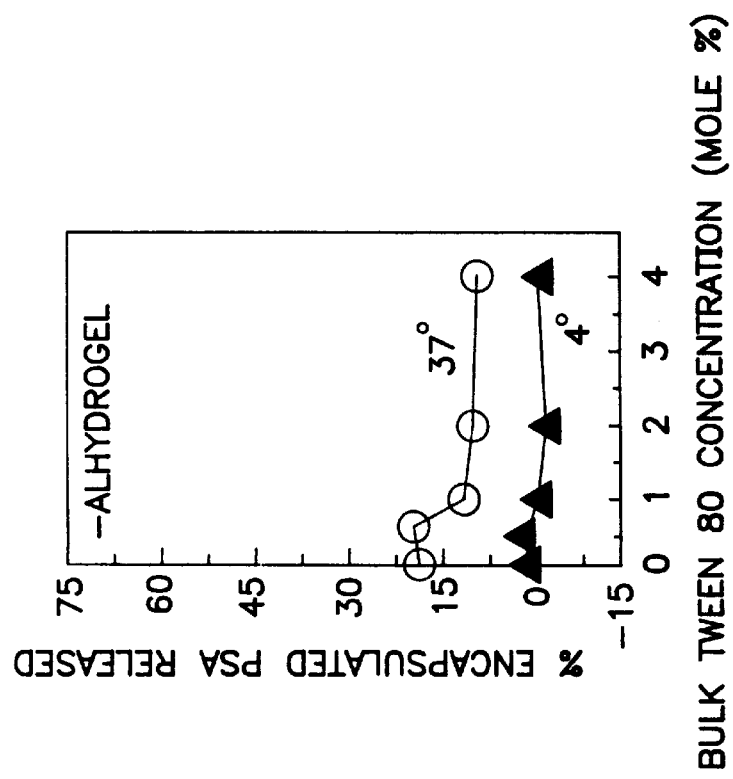
FIG. 4*a* shows the effect of Tween 80 concentration on release of PSA from liposomes at two temperatures in the absence of alum.
Figure 4C:
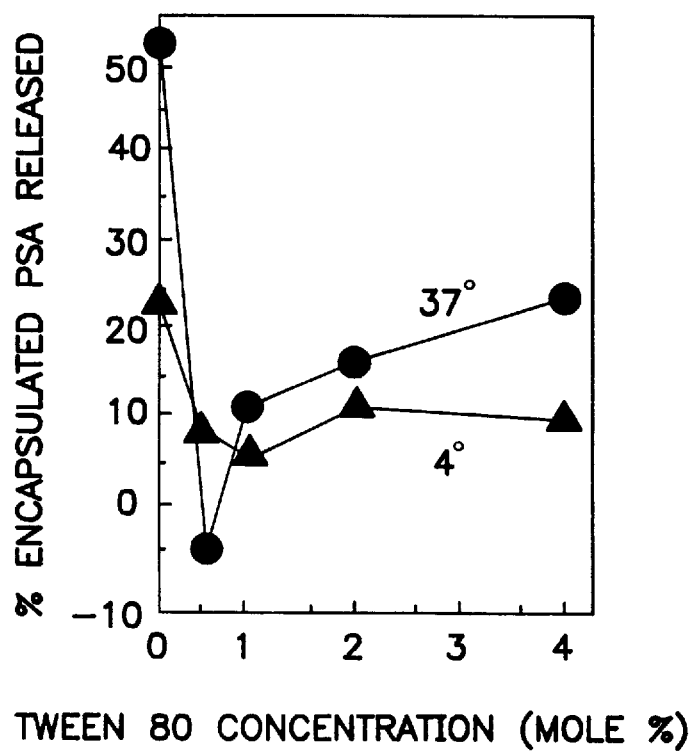
FIG. 4*c* represents the difference between FIGS. 4*b* and 4*a*.

The liposomes containing PSA were incubated with and without Alhydrogel™ in a 1/1 (v/v) ratio at 4° C., room temperature, and 37° C. As shown in FIGS. 1a and 1b, PSA was released linearly with time over a 14-day period in a temperature-dependent manner with or without alum, but the release of PSA was markedly enhanced in the presence of Alhydrogel™. FIG. 1c shows the release of PSA in the presence of the alum corrected for the release of PSA in its absence. Table 3 shows the calculated $V_{max}$ for comparison to the corresponding values for glucose. Comparison of the values in Table 3 with those in Table 2 shows that the rates of release induced by alum for PSA are an order of magnitude higher than those for glucose.

TABLE 3

Release of PSA

| | $V_{max}$ ($\mu$mole min$^{-1}$ × 10$^6$) | | |
|---|---|---|---|
| | 4° C. | RT | 37° C. |
| Alhydrogel ™ | 32.9 | 51.3 | 81.1 |

EXAMPLE 3

Effect of Phospholipid Composition on Liposome Integrity

It is known that liposomes comprising substantial quantities of unsaturated phospholipids or saturated phospholipids containing less than 14 carbon atoms in their esterified acyl chains are inherently unstable. Accordingly, when the experiment set forth in Example 2 was repeated by using DLPC (12C) or DOPC or DLnPC (unsaturated) as the phosphatidylcholine component, the effect of alum was undetectable since the liposomes were already unstable; when the liposomal preparation was incubated at 37° C., over 60% of the glucose was released in liposomes containing DMPC, DOPC or DLnPC even in the absence of Alhydrogel™. However, substituting DPPC or DSPC for DMPC in the liposomes gave no difference in rate of release from that measured with liposomes containing DMPC either with or without Alhydrogel™.

Various other liposomal preparations, designed to provide positively charged, negatively charged and neutral phospholipids were prepared generally as set forth in Example 1 and compared to the liposomes of Example 1 with respect to glucose release in the presence and absence of Alhydrogel™ at 37° C. for five days using the procedure described in Example 2. The results are shown in Table 4.

TABLE 4

Influence of Liposomal Phospholipid Charge on Destabilization of Liposome Permeability by Alhydrogel ™

| Phospholipid nature | Liposome composition | % Trapped glucose released | |
|---|---|---|---|
| | | −Alhydrogel ™ | +Alhydrogel ™ |
| Neutral phospholipid | (1) DMPC/CHOL/LA (10:7.5:0.11) | 1.69 | 9.50 |
| | (2) DMPC/CHOL (10:7.5) | 0.75 | 8.44 |
| Negatively charged phospholipid | (3) DMPC/DMPG/CHOL/LA (9:1:7.5:0.011) | 1.43 | 23.24 |
| | (4) DMPC/DMPG/CHOL (8:2:7.5) | −0.43 | 32.20 |
| Positively charged phospholipid | (5) DMPC/Stearylamine/CHOL (9:1:7.5) | 1.60 | 10.18 |
| | (6) DMPC/Stearylamine/CHOL/LA (9:1:7.5:0.011) | 2.02 | 19.95 |

In the absence of Alhydrogel™, all of the liposome preparations give comparable results. There appears to be some correlation of release, however, with the charge status of the phospholipid. For example, increasing the proportion of DMPG, a relatively negatively charged lipid, enhances the release (compare preparation 4 with preparation 3). Similarly, addition of the negatively charged LA enhances release in some instances (compare composition 6 with composition 5), although this is not consistent (compare composition 1 with composition 2).

EXAMPLE 4

Effect of Certain Detergents on Liposomal Stability

Various nonionic detergents were added to the liposome preparation at concentration levels up to 4 mole % and the resulting liposomes tested for stability in the presence and absence of Alhydrogel™ as measured by glucose release after incubation. The nonionic detergents tested included Span 80 and various Tweens. The results are shown in FIG. 2a–g. These data show that Tween 20, Tween 40, Tween 80 and Tween 85 were able to stabilize the liposomes in the presence of alum; Span 80, Tween 60 and Tween 65 were not.

Based on these results, it appears that the stabilizing detergent requires the polyoxyethylene side chains of the Tweens and at least one feature in the acyl group associated with destabilization of liposomes in general—i.e., either a relatively short acyl chain (<18C or at least one π-bond). These results are summarized in Table 5. In all cases, the successful stabilizing agent was most effective at a concentration of about 4 mole % (based on the liposomal lipid mixture).

TABLE 5

Effect of Detergent on Stability

| Detergent | Presence of side chain polyoxyethylene | No. Carbons in each acyl | No. π-bonds in each acyl | Stabilize wrt alum? |
|---|---|---|---|---|
| Tween 20 | + | 12 | 0 | + |
| Tween 40 | + | 16 | 0 | + |
| Tween 60 | + | 18 | 0 | − |
| Tween 65 | + | 18 | 0 | − |
| Tween 80 | + | 18 | 1 | + |
| Tween 85 | + | 18 | 1 | + |
| Span 80 | − | 18 | 1 | − |

Liposomal formulations prepared according to Example 1, either without Tween 80 or containing 4 mole % Tween 80, were assessed for integrity by glucose release in the presence of 1/1 v/v Alhydrogel™ incubated at 37° C. over a period of 120 hours. While the liposomes containing Tween 80 showed essentially no release of glucose, there was a substantial linear release of glucose over this time period in liposomes lacking Tween 80, as shown in FIG. 3. The calculated $V_{max}$ values in units of $\mu$M $min^{-1} \times 10^6$ are 0.44 for Tween 80-containing liposomes as compared to 23.4 for liposomes which do not contain Tween 80.

The experiments were repeated using varying concentrations of Tween 80 in liposomes prepared to encapsulate PSA, and incubation with and without Alhydrogel™ at 4° C. and 37° C. The results are shown in FIGS. 4*a* and 4b. FIG. 4*a* shows that the release of PSA from the prepared liposomes in the absence of alum is relatively independent of the presence or absence of Tween 80. On the other hand, FIG. 4*b* shows that in the presence of Alhydrogel™ Tween 80 is protective against release. FIG. 4*c* shows the results for various concentrations of Tween 80 included in the liposomes in the presence of Alhydrogel™ corrected for PSA release in its absence—i.e., FIG. 4*b* minus FIG. 4*a*. Maximal stabilization appears to occur in the range of 0.5–1 mole % Tween 80 when PSA is encapsulated.

We claim:

1. A pharmaceutical composition for eliciting an immune response comprising at least one antigen encapsulated in liposomes, said composition further comprising alum and at least one stabilizing agent in an amount effective to prevent the release of said antigen from said liposomes in the presence of alum, wherein said stabilizing agent is a nonionic detergent which is a polyoxyethylene sorbitan acylate, wherein the acyl moiety contains less than 18 carbons or said acyl moiety contains at least one π-bond.

2. The composition of claim 1, wherein said nonionic detergent is selected from the group consisting of Tween 20, which is polyoxyethylene sorbitan monolaurate; Tween 40, which is polyoxyethylene sorbitan monopalmitate; Tween 80, which is polyoxyethylene sorbitan monooleate; Tween 85, which is polyoxyethylene sorbitan trioleate; and mixtures thereof.

3. A composition for eliciting an immune response comprising at least one antigen encapsulated in liposomes, said composition further comprising alum and at least one stabilizing agent in an amount effective to prevent the release of said antigen from said liposomes in the presence of alum, wherein said antigen is prostate-specific antigen (PSA), and said stabilizing agent is a nonionic detergent which is a polyoxyethylene sorbitan acylate, wherein the acyl moiety contains less than 18 carbons or said acyl moiety contains at least one π-bond.

4. The composition of claim 2, wherein the nonionic detergent comprises Tween 80 which is polyoxyethylene sorbitan monooleate.

5. The composition of claim 1, wherein said liposomes are formulated from a mixture of dimyristoyl phosphatidylcholine, dimyristoyl phosphatidyl-glycerol, cholesterol, and lipid A.

6. The composition of claim 5, wherein the liposomes are formulated from a mixture of dimyristoyl phosphatidylcholine: dimyristoyl phosphatidyl-glycerol: cholesterol: lipid A in a mixture of 9:1:7.5:0.11.

7. The composition of any of claims 1–6, wherein the composition is prepared by reconstituting the liposomes in a reconstituting buffer containing said antigen and stabilizing agent.

8. The composition of any of claims 1–6, wherein the stabilizing agent is present in the liposomes at about 0.5–4 mole %.

* * * * *